United States Patent [19]
Matsushima

[11] Patent Number: 5,689,060
[45] Date of Patent: *Nov. 18, 1997

[54] HUMIDITY MEASURING DEVICE AND A HEAT COOKER EMPLOYING THE DEVICE

[75] Inventor: Haruo Matsushima, Yamatokoriyama, Japan

[73] Assignee: Matsushita Electric Industrial Co., Ltd., Osaka, Japan

[*] Notice: The term of this patent shall not extend beyond the expiration date of Pat. No. 5,387,254.

[21] Appl. No.: 724,146

[22] Filed: Sep. 30, 1996

Related U.S. Application Data

[63] Continuation of Ser. No. 642,080, May 1, 1996, abandoned, which is a continuation of Ser. No. 307,314, Sep. 16, 1994, abandoned, which is a continuation-in-part of Ser. No. 27,076, Mar. 5, 1993, Pat. No. 5,387,254.

[30] Foreign Application Priority Data

Mar. 6, 1992 [JP] Japan ................................ 4-49230
May 11, 1992 [JP] Japan ............................... 4-117118

[51] Int. Cl.⁶ ..................................................... G01N 29/02
[52] U.S. Cl. ..................... 73/24.04; 73/24.06; 73/29.05; 99/342; 219/707
[58] Field of Search ........................... 73/24.01, 24.06, 73/24.04, 24.05, 29.05, 29.01; 99/325, 332, 342; 219/707, 709

[56] References Cited

U.S. PATENT DOCUMENTS

| | | | |
|---|---|---|---|
| 3,839,616 | 10/1974 | Risman | 338/34 X |
| 3,848,457 | 11/1974 | Behymer | 73/24.01 |
| 4,255,964 | 3/1981 | Morison | 73/24.01 |
| 4,520,654 | 6/1985 | Terhune | 73/24.01 |
| 4,831,239 | 5/1989 | Ueda | 219/706 X |
| 4,864,088 | 9/1989 | Hiejima et al. | 219/707 |
| 4,876,889 | 10/1989 | Shakkottai et al. | 73/335.02 X |
| 5,060,507 | 10/1991 | Urmson et al. | 73/24.01 |
| 5,387,254 | 2/1995 | Matsushima | 73/24.04 |

FOREIGN PATENT DOCUMENTS

| | | | |
|---|---|---|---|
| 48-34585 | 5/1973 | Japan . | |
| 1290154 | 5/1985 | U.S.S.R. . | |
| 1250933 | 8/1986 | U.S.S.R. . | |
| 784146 | 10/1957 | United Kingdom | 73/24.01 |
| 798323 | 7/1958 | United Kingdom | 73/24.01 |
| 805544 | 12/1958 | United Kingdom | 73/24.01 |

*Primary Examiner*—Michael Brock

[57] ABSTRACT

A highly reliable, accurate humidity measuring device which detects differences in humidity between datum air and measuring air as a time or a phase difference in the propagation velocity of sonic waves, using sonic wave generating and receiving means, and processes this difference using circuitry to provide the humidity condition in the air being tested. Also an oven or heating cooker is disclosed equipped with the humidity measuring device so that it can detect the cooking condition of food by measuring temperature changes due to the steam generated from the food and then using the humidity measuring device to determine when to shut off the heat source of the oven.

17 Claims, 8 Drawing Sheets

HUMIDITY MEASURING DEVICE AND A HEAT COOKER EMPLOYING THE DEVICE

This application is a continuation of prior U.S. application Ser. No. 08/642,080 filed May 1, 1996, now abandoned, which is a continuation of application Ser. No. 08/307,314 filed Sep. 16, 1994, now abandoned, which is a continuation-in-part of application Ser. No. 08/027,076 filed Mar. 5, 1993, now U.S. Pat. No. 5,387,254.

FIELD OF THE INVENTION

The present invention relates in one aspect to a humidity measuring device which detects differences in humidity between datum air and measuring air as a time or a phase difference in the propagation velocity of audible sonic waves, using sonic wave generating and receiving means, and processes this difference using circuitry, and in another aspect to a heating cooker equipped with aforesaid humidity measuring device, which detects the cooking condition of food by measuring humidity changes due to the steam generated from food using aforesaid humidity measuring device, and controls or shuts off the heat source.

BACKGROUND OF THE INVENTION

Conventionally, a microwave oven, which is one example of a heat cooker, uses a humidity sensor with a semiconductor to detect cooking conditions and to control the heat source. In this example, the steam from the food which is heated dielectrically bonds to the semiconductor element in the humidity sensor, and the source of the electromagnetic waves is either controlled or shutoff by the electric signal generated by the element. However, this system had a reliability problem when cooking food due to oil and meat juice particles, not just the steam from food, which polluted the semiconductor. Even when periodically a burning process of this pollutant was attempted using a heater or the like, the electric signal from the sensor gradually changed, possibly becoming the cause for its deterioration or malfunction. In contrast to a humidity sensor with a semiconductor to detect humidity in the air, a method of measuring humidity by sonic waves is disclosed in Japanese Patent application, Kohkai Sho 48-34585. This method utilizes the characteristics that if there is a constant temperature, the velocity of the sonic waves going through the atmosphere becomes higher as the humidity becomes higher. Specifically, the method used is to place within a protected tubular body in which the humidity is to be measured an oscillator spaced from a microphone. A sonic wave is sent by the oscillator through the tubular body to the microphone and is then amplified. The amplified sonic wave is then sent to the oscillator within the tubular body so that the tubular body always has a sonic wave at a preselected frequency. The humidity in this tubular body is measured using the property that the velocity of the sound wave which varies with humidity provided the temperature is constant. This method of measuring humidity may solve the problem of sensor pollution. However, there is a problem of measuring the humidity under the condition when the temperature change is substantial, such as in a cooker, because the velocity change of the sonic waves is more affected by the temperature change than the humidity change.

U.S. Pat. No. 4,876,889 discloses an acoustic humidity sensor in which the water vapor content for air in drier ducts, ovens, furnaces and the like is determined by a measurement of sound speed which is done by measuring the time difference between sound pulses reflected by two reflectors spaced a known distance apart in a guide tube. The transmitter-receiver is located at one end of the tube. The tube has enough number of holes to allow the hot moist air to get into the probe tube. A non-porous tube containing dry air placed in the same duct provides a similar measurement of dry-sound speed. The ratio of the two speeds of sound or the two measured time intervals is a simple function of the water vapor content practically independent of temperature thereby providing a very accurate measurement of water vapor content over an extremely wide range of temperatures.

One object of the present invention is to provide a humidity measuring device with high precision and reliability, which comprises two chambers in which, an audible sonic wave oscillator or oscillators transmits to both chambers simultaneously and each chamber has a separate spaced apart audible sonic wave receiver.

Another object of the present invention is to provide a humidity measuring device that is ideally suited for use in a cooker or oven.

Another object of the present invention is to provide a humidity measuring device that is cost effective to produce and easy to use.

SUMMARY OF THE INVENTION

The invention relates to a humidity measuring device comprising a first acoustic chamber for accommodating reference air and a second acoustic chamber for accommodating air in which the humidity is to be determined, said chambers having a sonic wave absorbable material forming a wall of said chambers; a sonic wave generating means disposed at one end of said chambers; a sonic wave receiving means at the opposite end of each chamber and wherein the distance between the sonic wave generating means and the sonic wave receiving means in each chamber is the same; and a phase difference detecting means at the output of the sonic wave receiving means for both chambers to detect any difference in the phase of the sonic waves in the chambers so that said difference can be used to provide the humidity condition in the second chamber. Preferably the sonic wave could be an audible sonic wave of 15 to 20,000 cycles per second. Preferably, the two chambers will be in contact with each other and could be placed within a defined space so that the temperature would be substantially the same in both chambers.

Preferably, the chambers could be thermally conductive cylindrical chambers with the first containing reference air with essentially no moisture and the second chamber provided with small openings to allow the air to be tested to flow into and out of the second chamber. The humidity device of this invention is ideally suited for use in ovens such as microwave ovens, furnaces and any confined space.

The use of a sonic-wave absorbable material in the interior of the chambers is preferred since generating sonic waves in a chamber without the sound absorber material will generally result in reflected waves combining or mixing with the transmitted wave. This could result in the receiver means detecting an erroneous sonic wave pattern and when compared with the sonic wave pattern from the other chamber, could result in an inaccurate phase difference value being detected. With the use of the sonic absorber material in the chambers, the sonic wave generated will be detected substantially as transmitted. This will result in a more accurate phase different datum and therefore a more accurate measuring of the humidity condition in the air being sampled. In general, the sonic wave receiving means in both chambers have the same characteristics and are placed at an equal distance from the sonic wave generator means. The humidity difference between datum or reference air in one chamber and air to be tested in the other chamber is detected as the velocity difference of the sonic waves transmitted from a sonic wave generator such as an oscillator to each of the receivers. Any difference in the phase of the sonic waves is processed using circuitry which result in providing the humidity condition in the second chamber. This humidity measuring devise is ideally suitable to detect the condition of food in an oven by measuring the humidity change caused by the steam produced by the food and then controlling or shutting off the heat source, such as the electromagnetic wave generator in a microwave oven so that the food is not overcooked.

DESCRIPTION OF THE PREFERRED EMBODIMENTS

Figure 1A:
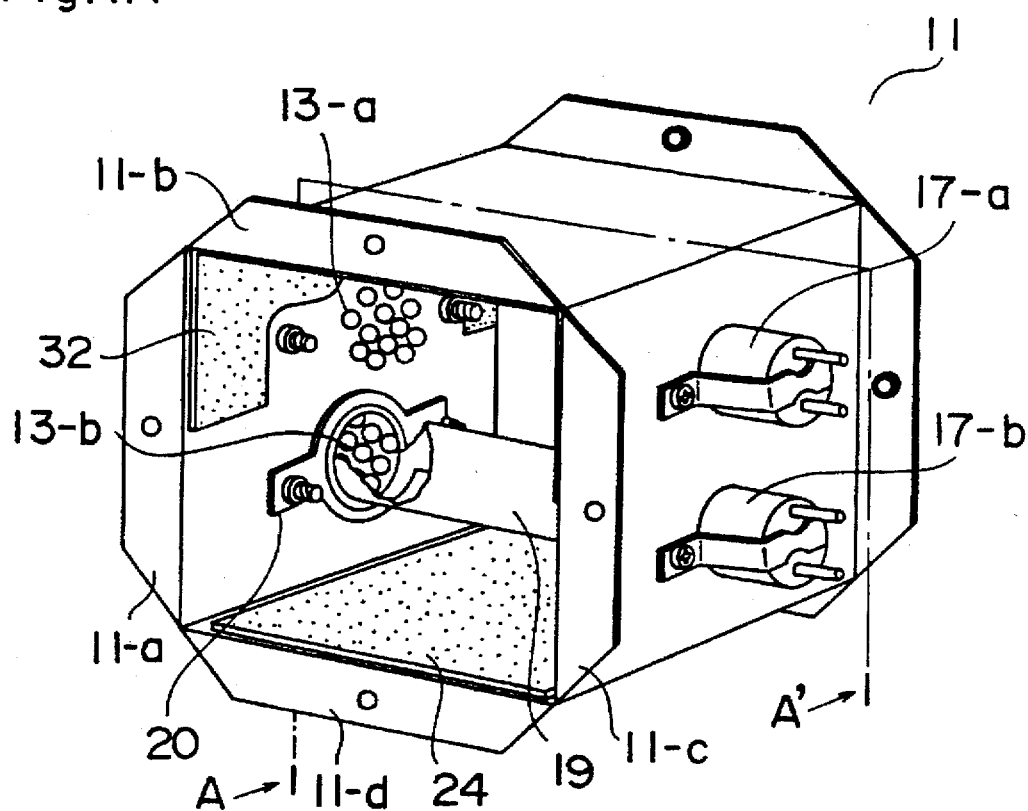
FIG. 1A is a perspective view of the humidity measuring device of the present invention in the example.
Figure 1B:
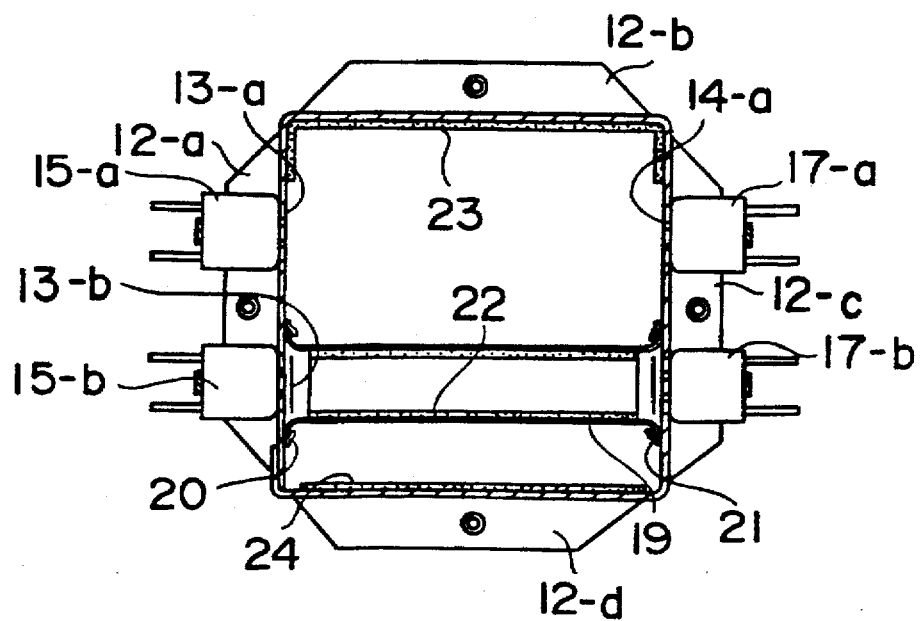
FIG. 1B is a cross-sectional view of section A–A' shown in FIG. 1A.
Figure 7:
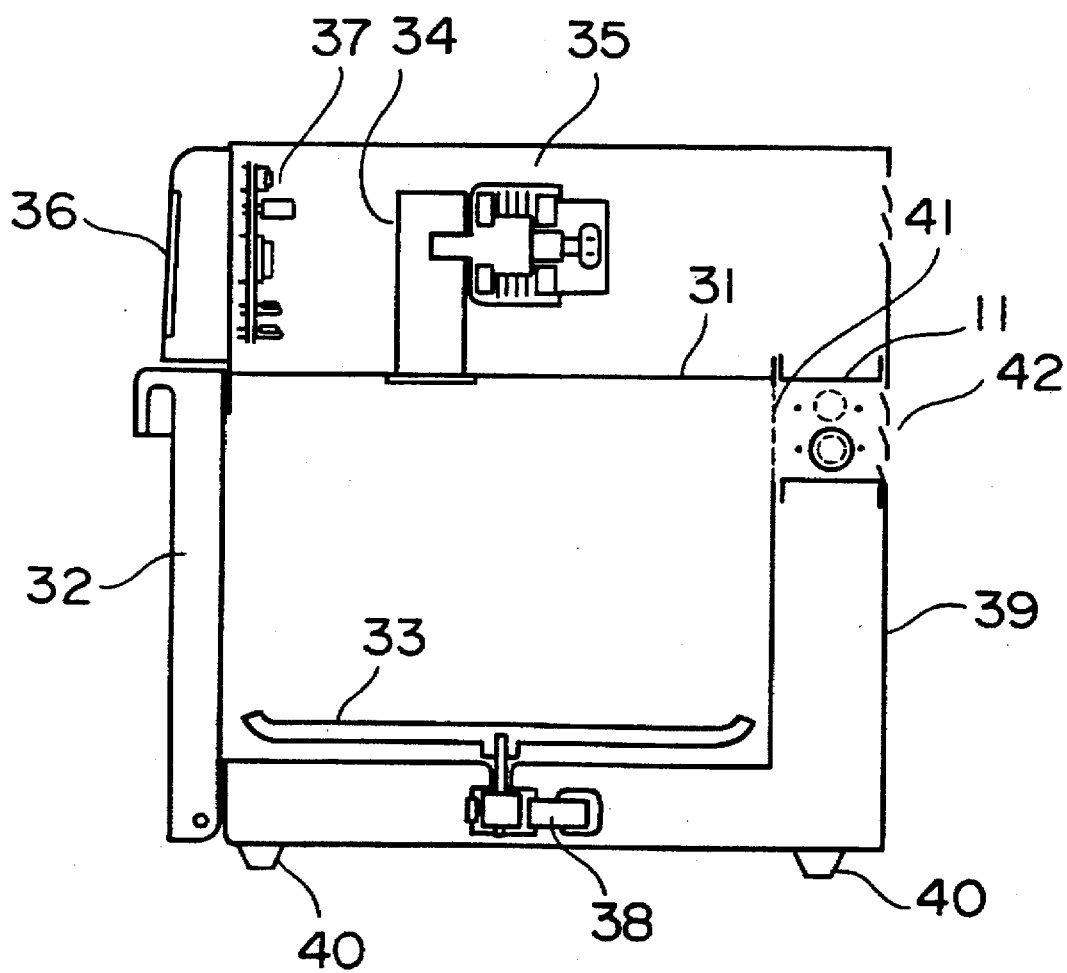
FIG. 7 is a cross-sectional view of the main parts of the cooker in the present invention.

FIG. 1A is a perspective view of one example of the humidity measuring device of the present invention where it can be placed in the exhaust passage of a cooker as shown in FIG. 7 and FIG. 1B is a cross section of view A–A'. The exhaust passage is of a square pipe shape 11 made of thin stainless steel, bent approximately 10 mm in width at both the top and bottom of the same planes (front and rear in FIG. 1A) designated 11-a, 11-b, 11-c and 11-d. The opposite side is similarly bent designated 12-a, 12-b, 12-c and 12-d on the same plane.

Both the right and left side of said square pipe have groups of small holes 13-a and 13-b (left side) and 14-a and 14-b (right side) within an approximate circle.

The right and left sides of said square pipe are parallel to each other, and 13-a and 14-a, and 13-b and 14-b face each other respectively. Sonic generating elements, 15-a and 15-b, which are calibrated to the same frequency at approximately 4 kHz are installed on the outside of the groups of holes on the left side of the square pipe using two screws each. Sonic receiving elements, 17-a and 17-b, which are calibrated to the same frequency at approximately 4 kHz are installed on the outside of the groups of holes on the right side of the square pipe using two screws each.

A thin aluminum cylindrical hollow pipe 19 of slightly larger diameter than the area of a group of small holes is placed in between said groups of small holes 13-b and 14-b inside the square pipe. Although a round cylindrical pipe is shown in the example, the shape can vary.

Each side of cylindrical pipe 19 hardly makes contact with the right and left interior walls of said square pipe, and the round pipe is fastened with no gaps in the left and right interior walls using flanges 20 and 21 with holes in the tabs and a hole which is slightly larger than that of aforesaid pipe. Sound absorber 22 made of polyurethane foam or the like is bonded inside pipe 19. Likewise the sound absorber 23 is installed on the interior surface of the top and part of the right and left interior walls of the square pipe, and sound absorber 24 is installed on the bottom.

Figure 2A:
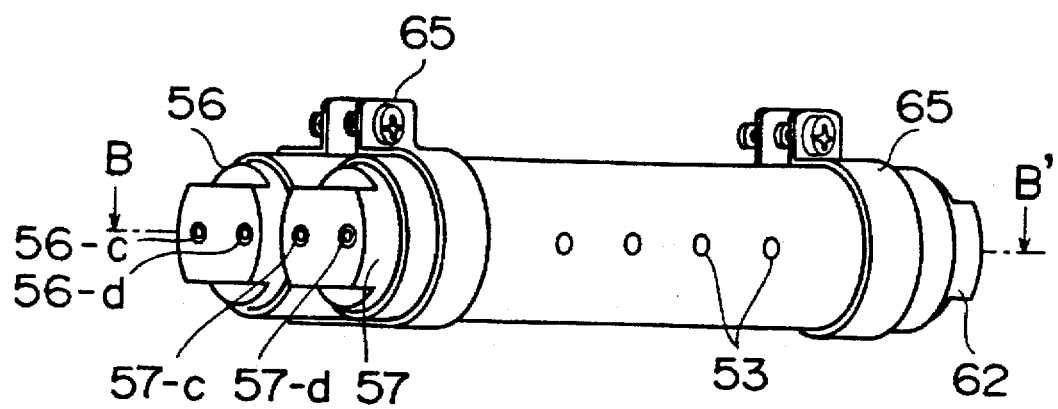
FIG. 2A is a perspective view of the humidity measuring device of the present invention in another example.
Figure 2B:
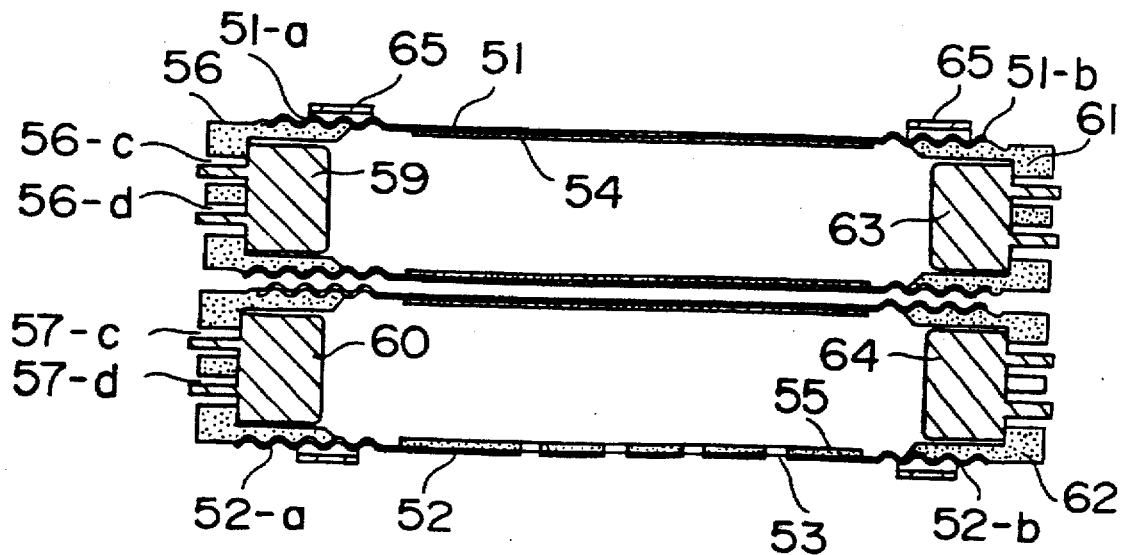
FIG. 2B is a cross-sectional view of the humidity measuring device of the present invention in another example shown in FIG. 2A.

FIG. 2A is another example of the present invention. In particular, it is perspective view and FIG. 2B is a cross-sectional view of B–B' when used in a humidity measuring device. Hollow materials (chambers) 51 and 52 are made of thin aluminum round pipes, and they are identical, with the exception of 52 having a small 53 on the side wall. Right-threads 51-a and 52-a are formed directly onto the interior walls of one end of the hollow materials 51 and 52, and left-threads 51-b and 52-b are formed likewise at the other end. Sound insulators 54 and 55 made of polyurethane foam or the like are inserted into the inside of hollow materials 51 and 52. Resin holders 56 and 57 for sonic generating elements are cylindrical containers, and the bottoms of the containers are partially cut out to form a U-shape. Furthermore, the other part of the outer rims 56 and 57 are threaded to match aforesaid right-threads 51-a and 52-a. Oscillating sonic generating elements 59 and 60 calibrated to the same frequency of approximately 4 kHz are installed inside the containers. Lead lines for the elements go through holes 56-c, 56-d, 57-c, and 57-d at the bottom of the containers. The holes are closed and the lead lines are secured by bonding after the lead lines go through the holes, and holders 56 and 57 for the generating elements are inserted by turning them clockwise into right-threads 51-a and 52-a of the hollow materials, respectively.

Resin holders 61 and 62 for the receiving elements are exactly the same as the holders for the sonic wave generating elements, except that they are threaded to match aforesaid left-threads 51-b and 52-b, and sonic wave receiving elements 63 and 64 with the same characteristics and resonating frequency of approximately 4 kHz, are installed inside the containers.

In addition, two hollow materials 51 and 52 are secured in contact with each other using metal bands 65 and two sets of screws, after adjusting the distance between the generating elements and the receiving elements. (The drawing of the cross-sectional view of the two materials shows the materials not touching each other for easier viewing purposes.)

Figure 3:
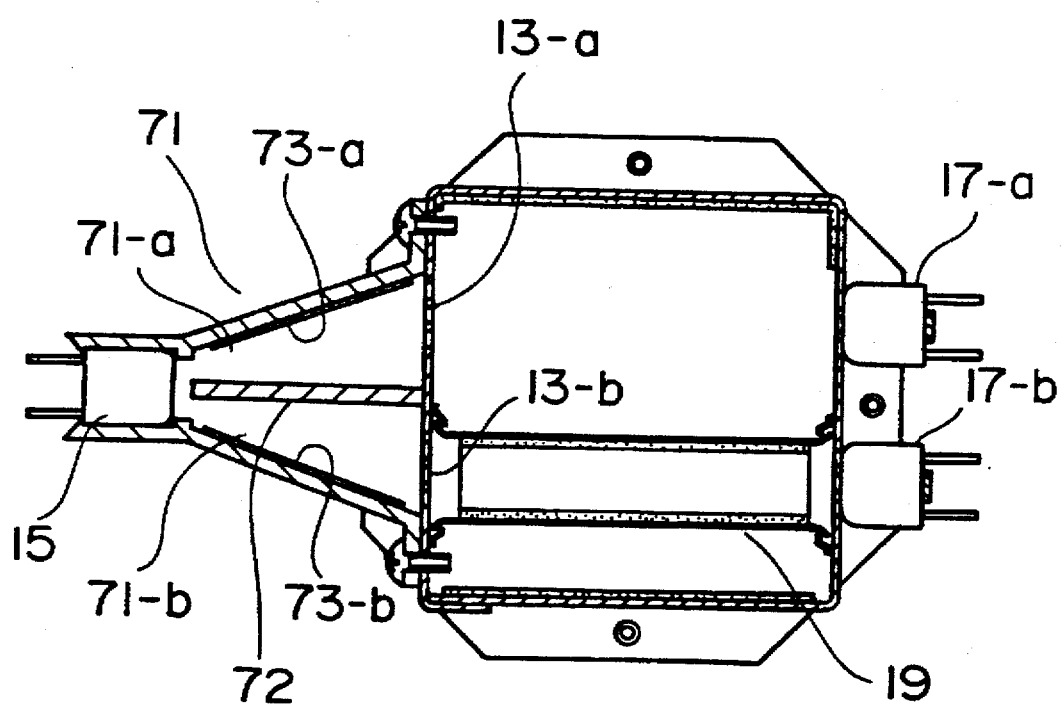
FIG. 3 is a cross-sectional view of the humidity measuring device of the present invention in another example.

In FIG. 3, a passage 71 is made of resin, and has a cone shaped hollow construction. Oscillating sonic wave generating element 15 is secured near the top of the cone, and the flat bottom of the cone should be large enough to cover both groups of holes 13-a and 13-b. Separator 72 is placed between the two groups of small holes, and extends from near the sonic wave generating element 15 to the bottom, dividing passage 71 into two symmetric passages, 71-a and 71-b, with separator 72 as the axis of symmetry. Passage 71 is symmetric with separator 72, an axis of symmetry. Sound absorbers 73-a and 73-b are bonded on to passages 71-a and 71-b respectively, and the passages are secured to exhaust passage 11 with two screws.

Figure 4:
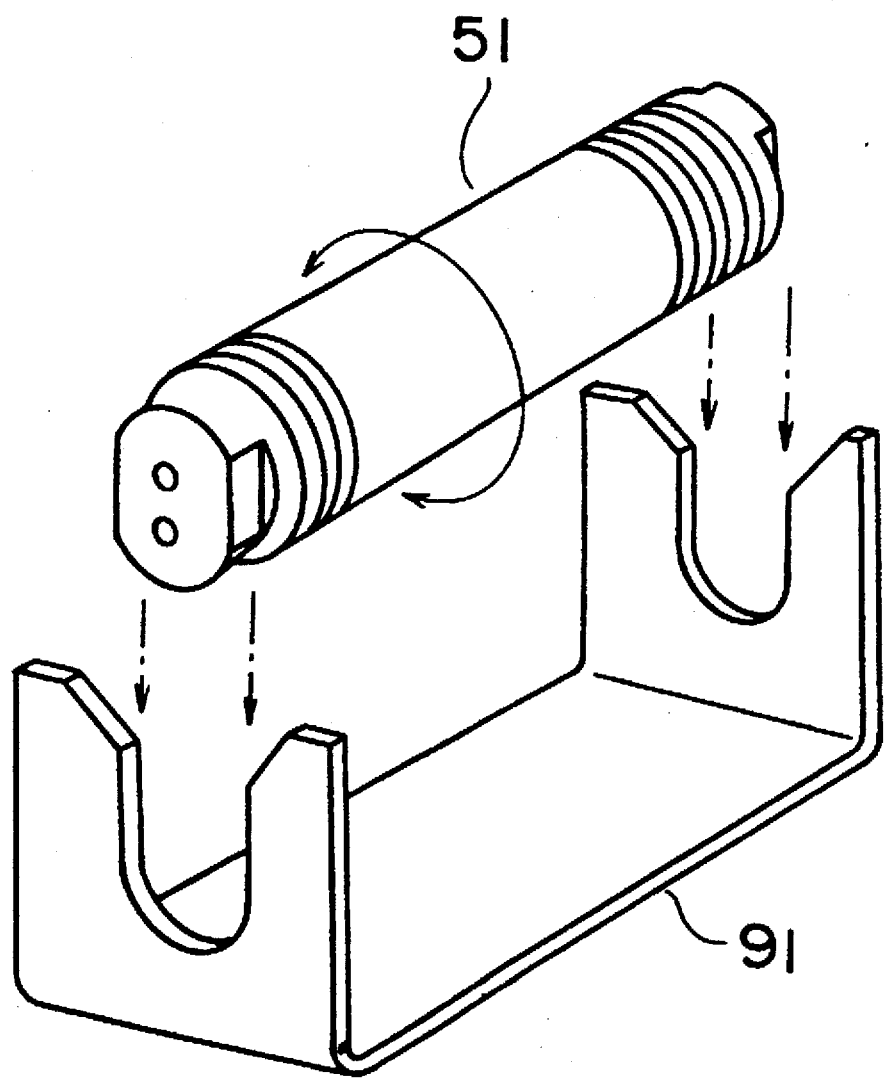
FIG. 4 is a perspective view of the adjustment work being done in the FIG. 2 example.

FIG. 4 is a perspective view to describe the adjustment in distance between the sonic wave generating elements 59 and 60 and the corresponding receiving elements 63 and 64, respectively shown in FIG. 2B. Adjuster 91 has a U-shaped cut-out on each end. The width of the U should be slightly larger than that of the U-shape on the bottom of the container for said generating and receiving element holders. Each end should be bent at a 90' angle and be parallel to each other. The holder for the generating element is inserted into one U-shaped cut-out, and the holder for the receiving element is inserted into the other U-shaped cut-out. The distance adjustment is made by turning the cylindrical hollow materials 51 or 52.

Figure 5A:
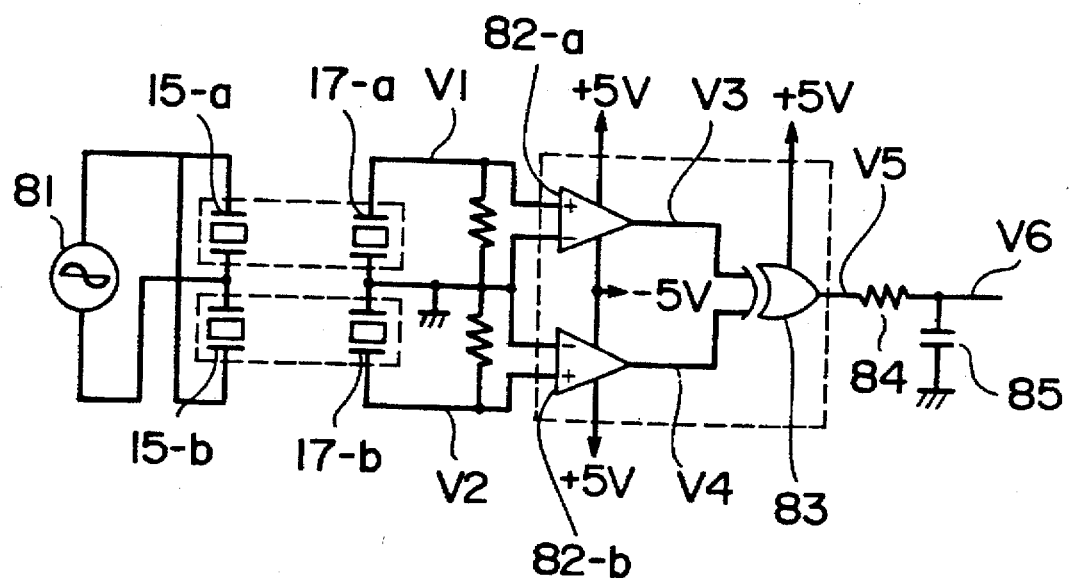
FIG. 5A is the voltage waves of electronic circuitry and other major parts employed in the humidity measuring device of the present invention.

FIG. 5A is the electronic circuit and waves of each part in the examples of the present invention. This electronic circuitry is combined with the examples in FIGS. 1A, 1B, 2A and 2B. For example, the output for generating element 81 with a frequency of 4 kHz is connected to two sonic wave generating elements, 15-a and 15-b shown in FIG. 1B (in the case of FIG. 2B connected to 59 and 60). Outputs for the two sonic receiving elements 17-a and 178-b shown in FIG. 1B (63 and 64 in FIG. 2B) are connected to the comparators 82-a and 82-b, and two outputs from the comparators, which are connected to the electric power source, are connected to an exclusive OR circuit 83. These outputs are connected to integrated circuit 86, which consists of resistor 84 and capacitor 85. The output signal wave, shown in 5B, of the sonic receiving element 17-a is referred to as V1; that of 17-b as V2; that of comparator 82-a as V3; that of 82-b as V4; and that of the exclusive OR circuit 83 as V5 with integrated circuit 86 being V6.

To explain the effect of aforesaid device, sonic waves of the same frequency and phase are generated due to output from generator 81 being added to two sonic generating elements 15-a and 15-b (or 59 and 60). These sonic waves are transmitted to exhaust passage 11, and reach ultrasonic receiving elements 17-a and 17-b (or 63 and 64). because the distances between both generating elements and receiving elements are the same, if the temperature and humidity inside and outside the cylindrical hollow material 19 are the same, then both receiving signals should be in the same phase. Hypothetically, the temperature is the same, but if the humidities inside and outside the hollow material 19 are different from each other, then a phase difference corresponding to the humidity difference will occur.

Figure 6:
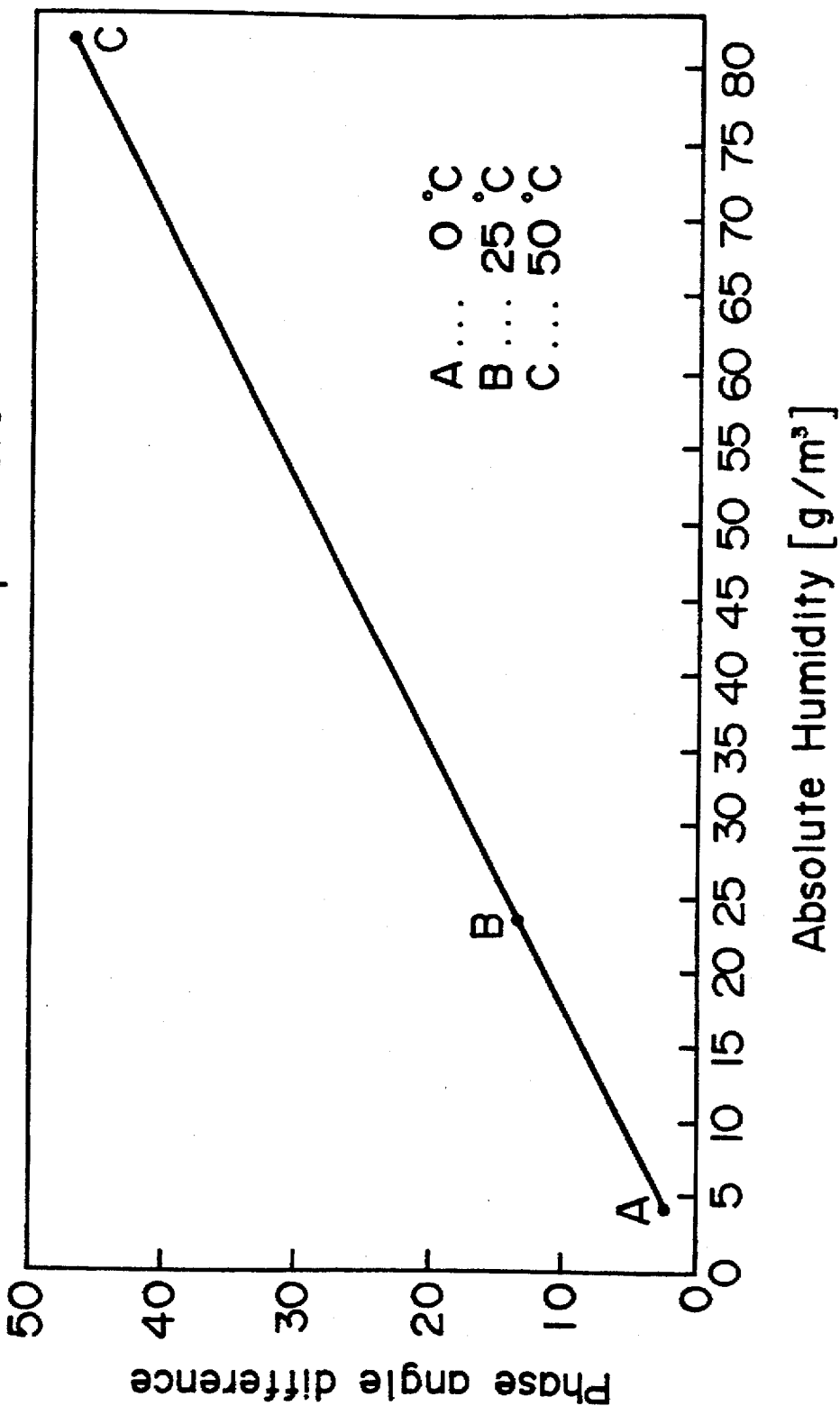
FIG. 6 is a graph indicating the correlation between the absolute humidity and phase difference in the examples in FIGS. 1 and 5.

In general, the sound velocity $C_w$ in the air of atmospheric pressure E with the steam of pressure P is acquired from sound velocity c in the dry air of the same temperature using the following formula:

$$C_w = c/\sqrt{\{1 - P/H(\gamma w/\gamma a - 0.622)\}}$$

Where $\gamma w$ denotes the ratio of specific heat at a constant pressure and specific heat at a constant volume of the steam, and likewise $\gamma a$ denotes the ratio of specific heat at a constant pressure and specific heat at a constant volume of the dry air. As is generally known, variation in the sound velocity due to a temperature change is proportional to the square root of the absolute temperature. FIG. 6 indicates the correlation between absolute humidity [$g/m^3$] and the phase angle difference at three different temperatures of 0° C., 25° C. and 50° C. In the embodiment shown in FIG. 1, hypothetically the frequency is 40 kHz and the distance between the generator and receiver is 6 cm. Since the saturated absolute humidities [$g/m^3$] are 4.85 at 0° C., 23.05 at 25° C. and 82.8 at 50° C., which are plotted as A, B and C respectively, they are linear within that range.

As this example indicates, if there is a humidity difference between the interior and exterior of hollow material 19, then a difference in receiving the signal waves between the two sonic wave receiving elements 17-a and 17-b will occur. In other words, the shapes of the waves V1 and V2 for 17-a and 17-b shown in FIG. 5B would show a phase difference. When this phase difference information is conveyed to the comparator, then only the rectangular waves V3 and V4 corresponding to the positive side of V1 and V2 are output. When these two are added to the exclusive OR circuit rectangular waves, V5, which only corresponds to the area where V3 and V4 do not overlap, is output. Thus, V5 is a rectangular wave which has exactly the same phase difference width for V1 and V2. When this information is conveyed to the integrated circuit, direct current voltage V6 proportional to the width of V5 is acquired.

Figure 5B:
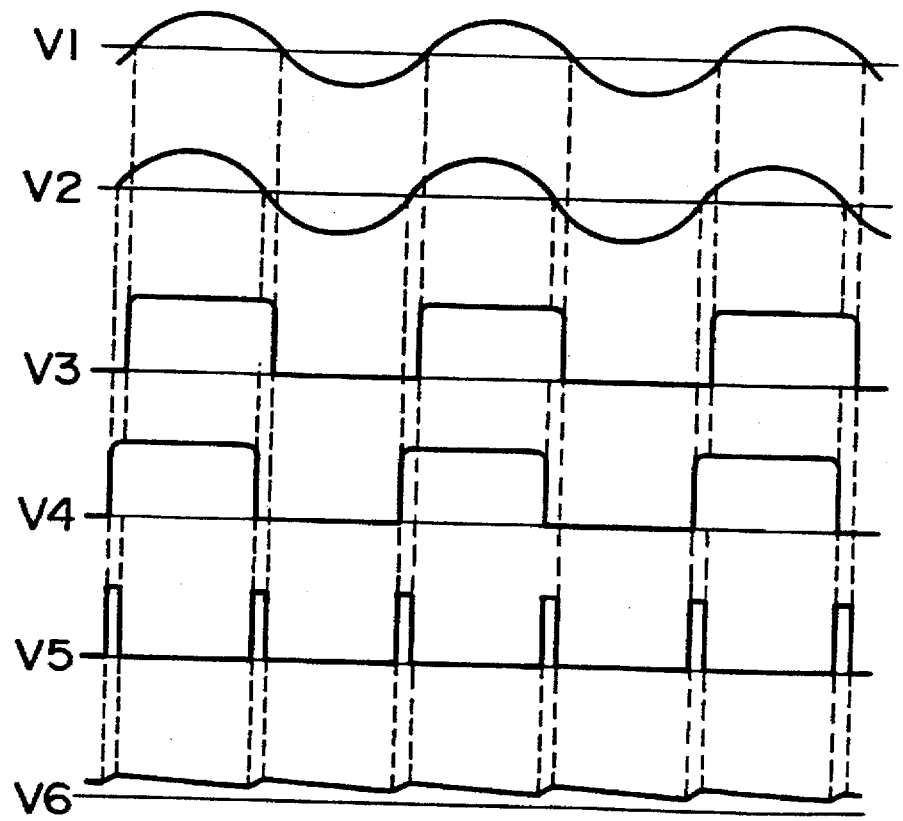
FIG. 5B is the output sine waves of circuit shown in FIG. 5A.

As shown in FIG. 5B, the maximum phase shift for measuring is ¼ of the wave length of the wave employed. Using the exclusive OR gate circuit, the output voltage V6 varies as a sinusoidal curve, such that V6=E|sin X| where E is a constant and X is the phase difference corresponding to the absolute humidity. Accordingly, an input with more phase difference than ¼ wave length can not be distinguished from the input of a wave equal to a less than ¼ wave length. Thus it takes 6.25 μs for an ultrasonic wave of 40 kHz to propagate ¼ wave length assuming 370 m/s of sound velocity. Assuming the distance between the sound source and the receiving point to be 6 cm, the velocity of the sound wave is 382 m/s at 40 kHz which is 6.25 μs faster than the reference velocity of 370 m/s. The absolute humidity corresponding to this velocity difference is calculated from the formulas above and found to be 150 $g/m^3$. Consequently, at this value of humidity, the output V6 reaches the top sine wave and therefore, the variation of humidity for 130 to 150 $g/m^3$ does not result in an appreciable change of the output voltage. As some margin is necessary using conventional devices, 80 $g/m^3$ is believed to be the maximum humidity for ultrasonic waves of 40 kHz or more. Contrary to this, with 4 kHz audio waves, it is possible to measure up to 800 $g/m^2$ or 10 times greater than for 40 kHz waves. This 4 kHz wave can be used to detect humidity as high as 350 $g/m^2$ in a confined space. However, measure precision declines with 4 kHz compared with 40 kHz but lower frequency waves are preferred for the measurements with a wide range of variations as can exist in conventional electronic ranges.

The microwave oven shown in FIG. 7 contains door 32, plate 33, display panel 36, circuitry 37, heating element 34-35, top wall 31, back wall 39, motor element 38, and support legs 40. In the microwave oven when food is heated in a heating chamber, steam is generated, and the steam is exhausted through a group of small holes 41 located in the back of the heating chamber, exhaust passage 11 and a group of louvers located in the back of the exterior box. When the steam goes through exhaust passage 11, there is a humidity difference between the interior and exterior of hollow material 19, since the steam only passes the exterior of the cylindrical hollow material 19. This difference, as aforementioned, is converted into direct voltage, and added to the control measure as humidity information.

As indicated in FIG. 3, an example with an omission of one sonic wave generating element works as well. In this case, the possibility of the steam from food entering the inside of hollow material 19 through a group of 13-a and 13-b when passing the exhaust passage may be a concern.

However, in actuality, as long as the exhaust resistance of the group louvers 42 is controlled under the resistance of a group of small holes 13-a this effect need not be of concern. In addition, when the chamber condition is either low in both temperature and humidity or high in both temperature and humidity one concern is that the information on steam generated from food may vary substantially. However, the humidity variance in the steam from food is significantly large, thus, there is no effect on acquiring information. For example, hypothetically if 150 g of cauliflower is heated for 2 minutes, and 7 grams of water is evaporated in a heating chamber of 20 liters, then the accumulated absolute humidity for 2 minutes is 350 g/m$^3$ and humidity atmosphere of 30° C. with 100% relative humidity being 30.3 g/m$^3$.

Figure 8:
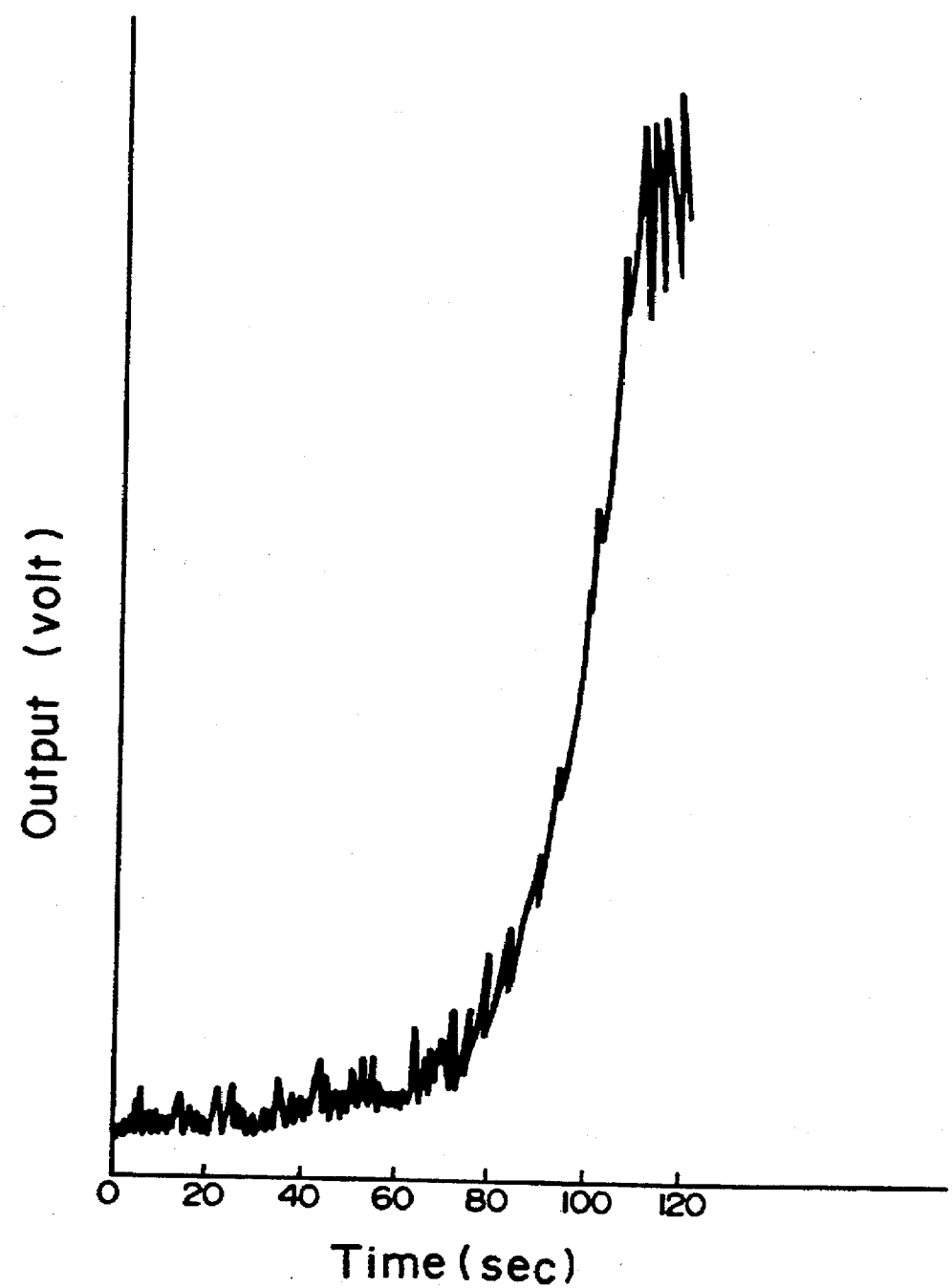
FIG. 8 is a graph indicating the results of measurement when a vegetable was cooked as in the FIG. 7 example.

FIG. 8 is an example of the actual measurements. This measurement output (voltage) is indicated in FIG. 5B was recorded by a pen recorder. When the cauliflower was being heated using the electronic circuit described in FIG. 5A inside the microwave oven shown in FIG. 7, a large variance amount was achieved in an increment within seconds.

The example shown in FIGS. 2A and 2B is given to determine the absolute humidity value, and the difference in propagation velocities of sonic waves between the interior and exterior of hollow chamber 51. Small holes 53 were drilled in order to achieve the task. Hollow chamber 52 (in exactly the same shape as 51 with the exception of the small holes) and chamber 51 making contact was secured With band 65 made of a thin aluminum plate with high heat conductivity in order to equally conduct the ambient temperature changes to both materials of hollow the chambers 51 and 52. Only steam enters the interior of chamber 52 through small holes 53. There may be a transient temperature difference between 51 and 52 due to the heat which the steam contains. However, hollow chamber 51 is not only in contact with 52 but also in contact with the atmosphere, and the temperature difference gradually becomes less.

As an accurate measuring method for the absolute humidity value, for example, a wet and dry bulb hygrometer with airing is available. However, it takes approximately 10 minutes to take an accurate measurement of the humidity. In accordance with the example of the present invention, it is possible to measure the humidity within seconds if the temperature is stabilized quickly. As an adjustment task, first, dry air is injected into the inside of hollow chamber 51, for example, and the saturated steam amount in −30° C. is 1 g/m$^3$ or less, and installation into the holder for generating element 56 and for receiving element 61 at a lower temperature which was followed by distance calibration work similar to that of FIG. 4 aforementioned. This distance calibration was conducted by connecting hollow materials 51 and 52 separately to the electronic circuit shown in FIG. 5A, and adjusting until the voltage V6 becomes 0, then sealing and securing with adhesive or the like.

Dry air is sealed inside hollow material 51 after aforementioned assembly and work, and ambient air with humidity which is the measuring object enters into hollow material 52. Furthermore, the temperatures in hollow materials 51 and 52 are equal, thus absolute humidity [g/m$^3$] can be obtained by measuring the voltage indicated in FIG. 5A and 5B, and using the correlation which is shown in FIG. 6.

In accordance with the present invention, the physical phenomenon is directly measured and taken out as electrical signals, then humidity in the measuring air could easily be measured with a high degree of accuracy and automatically even at a distance. Therefore, it becomes possible to control the humidity using the electric signals obtained.

Because this method directly measures the basic physical phenomenon, accuracy in measurement is superior. For example, a heated room interior on a cold winter day has very low humidity. If this humidity is measured using a dry and wet bulb hygrometer, airing for 10 minutes, a small amount of humidity which was evaporated from the hygrometer will increase the amount of humidity in the closed room, and the humidity value may be measured different from the initial humidity. On the other hand, according to the present invention, the accurate humidity is measured because no humidity is generated during the process.

When applied to a heat cooker, even if the sensor in the humidity measuring device is exposed to various types of gases and particles from food, there is no change in effect on the element of propagation velocity of the sonic wave in the air. Furthermore, even if the amplitude of the sonic waves caused a small change, there is no element which is affected by the change; consequently, there are no elongating changes in the measured values. Furthermore, regarding the fast response time of humidity measurement, in particular, as indicated in the examples in FIG. 1A or 3, once humidity enters inside exhaust passage 11, the humidity can be measured in an order of seconds, which enables automatic cooking at the proper temperature and length of time even when reheating cold food or cooking when requiring fine adjustments.

Although a microwave oven was given as an example for a heat cooker herein, the heat source is not limited to electromagnetic generators such as the Magnetron.

What is claimed:

1. An oven containing a humidity measuring device comprising a first hollow chamber for accommodating reference air and a second hollow chamber for accommodating air in which the humidity in the second hollow chamber is to be determined, each of said hollow chambers being made of a thin high thermally conductive material and having a sonic wave absorbable material forming a wall of said chambers, such sonic wave absorbable material being capable of effectively absorbing reflected waves so that the sonic wave to be generated will be detected substantially as transmitted; the first chamber is disposed within the second chamber; a sonic wave generating means disposed at one end of said chambers; a separate sonic wave receiving means at the opposite end of each hollow chamber in which the distance between the sonic wave generating means and the sonic wave receiving means of each chamber is the same; and a phase difference detecting means at the output of the sonic wave receiving means from both chambers to detect any difference in the phase of the sonic waves in the chambers so that said difference will be used to determine the humidity condition in the second chamber.

2. The oven of claim 1 wherein said chambers of the humidity measuring device are cylindrical chambers.

3. The oven of claim 2 wherein the thermally conductive material is aluminum.

4. The oven of claims 1 wherein each chamber of the humidity measuring device has a separate sonic wave generating means.

5. The oven of claim 1 wherein the sonic wave generating means is an oscillator.

6. The oven of claim 1 wherein said first chamber is adapted to contain reference air sealed within said first chamber and said second chamber has at least one opening to permit air to be tested to flow into and out of said second chamber.

7. The oven of claim 6 wherein each chamber has a separate sonic wave generating means.

8. The oven of claim 1 wherein the phase different detecting means comprises two comparator circuits and an exclusive OR gate.

9. The oven of claim 1 wherein said oven has an exhaust area and said humidity measuring device is positioned within said exhaust area.

10. The oven of claim 1 wherein the thermally conductive material is aluminum.

11. A method for determining the humidity within an oven comprising the steps:

(a) preparing an oven and placing within said oven a humidity measuring device comprising a first hollow chamber for accommodating reference air and a second hollow chamber for accommodating air in which the humidity in the second chamber is to be determined, each of said chambers being made of a high thermally conductive material and having a sonic wave absorbable material forming a wall of said hollow chambers, such sonic wave absorbable material being capable of effectively absorbing reflected waves so that the sonic wave to be generated will be detected substantially as transmitted; the first chamber is disposed within the second chamber; a sonic wave generating means disposed at one end of said hollow chambers; a separate sonic wave receiving means at the opposite end of each hollow chamber in which the distance between the sonic wave generating means and the sonic wave receiving means of each hollow chamber is the same; and a phase difference detecting means at the output of the sonic wave receiving means from both chambers;

(b) placing referenced air within the first chamber and supplying air from within the oven through the second chamber;

(c) maintaining the temperature within each hollow chamber substantially the same;

(d) generating a sonic wave through said first chamber and said second chamber;

(e) detecting the sonic waves transmitted through each chamber at the end of said first chamber and said second chamber; and (f) detecting any difference in the phase difference detecting means of the sonic waves at the end of each hollow chamber so that the difference is used to provide the humidity conditions in the second hollow chamber.

12. The process of claim 11 wherein said chambers are cylindrical chambers.

13. The method of claim 11 wherein each chamber has a separate sonic wave generating means.

14. The method of claim 11 wherein the sonic wave generating means is an oscillator.

15. The method of claim 11 wherein the oven has exhaust area and said humidity measuring device is positioned within the exhaust area.

16. The method of claim 15 wherein the second chamber is disposed within the first chamber.

17. The method of claim 11 wherein the thermally conductive material is aluminum.

* * * * *